US012766929B2

(12) United States Patent
Guggenheim

(10) Patent No.: US 12,766,929 B2
(45) Date of Patent: Oct. 20, 2026

(54) SCENTING DEVICE FOR A VEHICLE

(71) Applicant: Supair-Tel AG, Glattbrugg (CH)

(72) Inventor: Rudolf Heinrich Guggenheim, Wollerau (CH)

(73) Assignee: SUPAIR-TEL AG, Glattbrugg (CH)

( * ) Notice: Subject to any disclaimer, the term of this patent is extended or adjusted under 35 U.S.C. 154(b) by 855 days.

(21) Appl. No.: 17/900,268

(22) Filed: Aug. 31, 2022

(65) Prior Publication Data

US 2023/0067503 A1 Mar. 2, 2023

(30) Foreign Application Priority Data

Sep. 1, 2021 (EP) .................................... 21194251

(51) Int. Cl.
*B60H 3/00* (2006.01)
*A61L 9/12* (2006.01)

(52) U.S. Cl.
CPC .............. *B60H 3/0028* (2013.01); *A61L 9/12* (2013.01); *A61L 2209/15* (2013.01)

(58) Field of Classification Search
None
See application file for complete search history.

(56) References Cited

U.S. PATENT DOCUMENTS 10,500,299 B2 12/2019 Lalo
11,059,353 B1 * 7/2021 Bennett .................. A61L 9/012
2009/0230210 A1 * 9/2009 Wang .................. B60H 3/0028 239/57
2014/0051344 A1 * 2/2014 Guggenheim ............ A61L 9/12 454/157
2018/0140735 A1 * 5/2018 Lalo ..................... B60H 3/0028

FOREIGN PATENT DOCUMENTS

CH 709702 A2 11/2015
DE 102011001637 A1 10/2011
KR 20190000337 U 2/2019
WO WO-2015179992 A1 * 12/2015 ........... B60H 3/0028

OTHER PUBLICATIONS

Guggenheim et al. WO2015179992A1-translated document (Year: 2015).*
Guggenheim, R. WO2015179992A1-translated document (Year: 2015).*
Search Report from corresponding European Application No. 21194251.1, Feb. 14, 2022.

* cited by examiner

*Primary Examiner* — Jelitza M Perez
(74) *Attorney, Agent, or Firm* — Workman Nydegger

(57) ABSTRACT

A scenting device is provided for scenting the interior of a vehicle. The scenting device comprises a housing, a scent container arranged in the housing and at least one coupling device arranged on the housing. At least one holding device can be coupled to the coupling device. By means of the holding device, the scenting device can be attached to a ventilation in the interior of the vehicle.

13 Claims, 3 Drawing Sheets

SCENTING DEVICE FOR A VEHICLE

FIELD OF THE INVENTION

The invention relates to a scenting device for a vehicle with a housing and a scent container arranged in the housing. Furthermore, the scenting device comprises at least one coupling device which is arranged on the housing and at least one holding device for attaching the scenting device to a ventilation in the interior of a vehicle.

BACKGROUND

Scenting devices are known which can be suspended in the interior of a vehicle and have, for example, a material impregnated with a scent. Such devices can be manufactured at low cost, but their scenting effect can be uneven and the scenting body, which is usually suspended from the interior rear-view mirror, can disturb visibility.

Furthermore, containers with scent are known which are attached to a ventilation grille in the interior of a vehicle. The container for the scent has inlet openings so that air from the ventilation flows into the container, comes into contact with the scent and, enriched with scent molecules, leaves the container through outlet openings. Such containers can be attached to and removed from the ventilation grille by means of a clamping part.

SUMMARY

The object is to provide a scenting device that can be used in a variety of ways.

The object is solved by a scenting device for a vehicle with the features of claim 1. The term "vehicle" includes land vehicles, such as passenger cars and trucks, and also aircrafts.

The scenting device according to the invention comprises a housing in which a scent container is arranged. At least one coupling device is arranged on the housing. Furthermore, the scenting device comprises at least one holding device for attaching the scenting device to a ventilation in the interior of the vehicle. The holding device can be coupled to and decoupled from the coupling device. Thus, the holding device can be coupled to and decoupled from the housing.

The possibility of decoupling the holding device from the housing has the advantage that different types of a holding device can be mounted on the housing. The scenting device can thus be fixed to different ventilation, it can be used flexibly and is user-friendly. In addition, used holding devices can also be replaced with new holding devices in a simple manner without having to replace the entire scenting device.

Advantageously, at least three coupling devices can be arranged on the housing. One of the at least one holding device can be coupled to each coupling device.

Depending on the holding device and the ventilation, it is not sufficient to mount the scenting device on the ventilation with only one holding device. For example, the scenting device can be mounted on the ventilation with two holding devices simultaneously. Furthermore, depending on the type of holding device, it may be necessary to mount them at different positions on the housing. Therefore, several coupling devices are provided in order to be able to couple the holding devices to the housing at different positions.

Advantageously, the three coupling devices are spaced apart from each other and/or inlet openings can be provided between the at least three coupling devices, through which air can flow into the housing.

In particular, the coupling device and the holding device are configured to couple together in the form of a snap-fit. A "snap-fit" is a connection in which the coupling device and the holding device are form-fit joined. During the creation of the snap-fit, one of the components, in particular the coupling device, deforms elastically and then hooks releasably in the form of a form-fit connection.

With the idea of being able to couple different holding devices to the housing of the coupling device, a snap-fit between the holding device and the coupling device is shown to be a suitable solution so that the user can easily detach the holding device from the coupling device and couple it to the coupling device.

Advantageously, the coupling device comprises a frame and the holding device comprises a flat plate, configured such that the plate of the holding device can be slid under the frame of the coupling device for coupling, in particular wherein the plate has at least one protrusion which engages in gaps of the frame in the coupled position.

Advantageously, the scenting device comprises at least two structurally differently designed holding devices, i.e., two different types of holding devices. The at least two structurally different holding devices can each be coupled to at least one of the at least one coupling device.

This can be designed such that each possible holding device can be fixed on each coupling device. However, it may also be such that one type of holding device can only be coupled to one or more particular coupling devices, but not to all coupling devices. "Structurally different" means that the at least two holding devices are not identical, but are configured or shaped differently. In particular, the at least two holding devices adhere to the ventilation in the interior of the vehicle by means of different technical principles. This makes it possible to attach the scenting device to different types or shapes of ventilation. The scenting device can be used flexibly by the user.

In a particular embodiment, one of the at least one holding device comprises a rubber cap. In particular, the rubber cap is configured to be clampable between two slats of the ventilation, and/or the rubber cap is removable from the holding device.

The rubber cap may comprise as material silicone, rubber and/or an elastomer, in particular a thermoplastic elastomer. In particular, it may comprise a material having a hardness in the range of 30 Shore-A to 90 Shore-A.

A rubber cap, due to its elasticity, allows for easy mounting of the scenting device to the ventilation in the vehicle. The rubber cap is elastic and can adapt to different dimensions of a ventilation. In addition, the elasticity allows the rubber cap to be clamped between two slats of the ventilation.

Advantageously, the scenting device comprises at least two holding devices with rubber caps of different sizes. The user can thus choose to mount a larger or smaller rubber cap, depending on the design of the ventilation. If the slats of the ventilation are more spaced apart, the user couples a holding device with a larger rubber cap to the housing of the scenting device. However, if the slats are less spaced apart, the user chooses a holding device with a smaller rubber cap. Thus, different holding devices with different rubber caps can be supplied with a scenting device, which the user can selectively mount on the housing.

Advantageously, the rubber cap comprises an outer surface, a base surface and an upper surface opposite the base surface. Depending on the design of the rubber cap, the upper surface may be part of the outer surface. The base surface is the surface of the rubber cap which, in the assembled state, faces the housing of the scenting device. The upper surface is the surface of the rubber cap which, in the assembled state, faces away from the housing of the scenting device. For better understanding, the defined surfaces are visualised in the figures.

In particular, a groove is arranged on the upper side of the rubber cap and/or two upper edges running parallel are arranged on the upper side of the rubber cap, in particular wherein the two upper edges each have a rectilinear section.

A groove leads to an improved elastic behaviour of the rubber cap. The rubber, in particular the upper edges, can move into the free space of the groove and thus show a better elastic behaviour.

Advantageously, the edge line of the base surface has at least one, in particular two, rectilinear sections. The base surface is thus not exclusively round or elliptical in shape, but also includes rectilinear sections. Straight-line sections have the advantage that the contact surface with the ventilation, in particular the ventilation slats, is larger, and thus a better clamping effect can be achieved between the scenting device and the ventilation.

In particular, the edge line comprises two half circles or half ellipses connecting the two rectilinear sections.

In a further embodiment, at least one of the holding devices may comprise a spreader element. A holding device with a spreader element is, in addition to a holding device with a rubber cap, another structurally different type of holding device.

In particular, the scenting device can be delivered with both a holding device with a spreader element and a holding device with a rubber cap. This provides the user with different holding devices with different technical principles. It is easier for the user to mount the scenting device on differently designed ventilation because he has different holding devices available.

In particular, the spreader element is designed such that it can be clamped between two slats of the ventilation, and/or the spreader element can have at least two spreader members.

Advantageously, the holding device with the rubber cap and the holding device with the spreader element can be coupled to all coupling devices. This gives the user maximum flexibility in attaching the holding devices to the housing.

In a particular embodiment, exactly three coupling devices are arranged on the housing. One of the three coupling devices is arranged in the middle between the other two outer coupling devices.

In a first configuration, only the coupling device arranged in the middle is coupled to one of the at least one holding device, in particular a holding device with a spreader element. In a second configuration, only the outer two coupling devices are coupled to one of the at least one holding device, in particular to two holding elements each having a rubber cap. In the second configuration, holding elements with smaller or larger rubber caps can be coupled.

BRIEF DESCRIPTION OF THE DRAWINGS

Further embodiments, advantages and applications of the invention will be apparent from the dependent claims and from the following description based on the figures. The figures show:

DETAILED DESCRIPTION OF THE INVENTION

Overview

FIGS. 1 to 4 show a scenting device 1 according to the invention for a vehicle with a housing 2 and a scent container 3 arranged in the housing 2. The scent container 3 is replaceable. It can be removed from the housing 2 and a new scent container 3 can be inserted into the housing 2. The scenting device 1 has holding devices 4 with which the scenting device 1 can be mounted on a ventilation in the interior of the vehicle.

Figure 1:
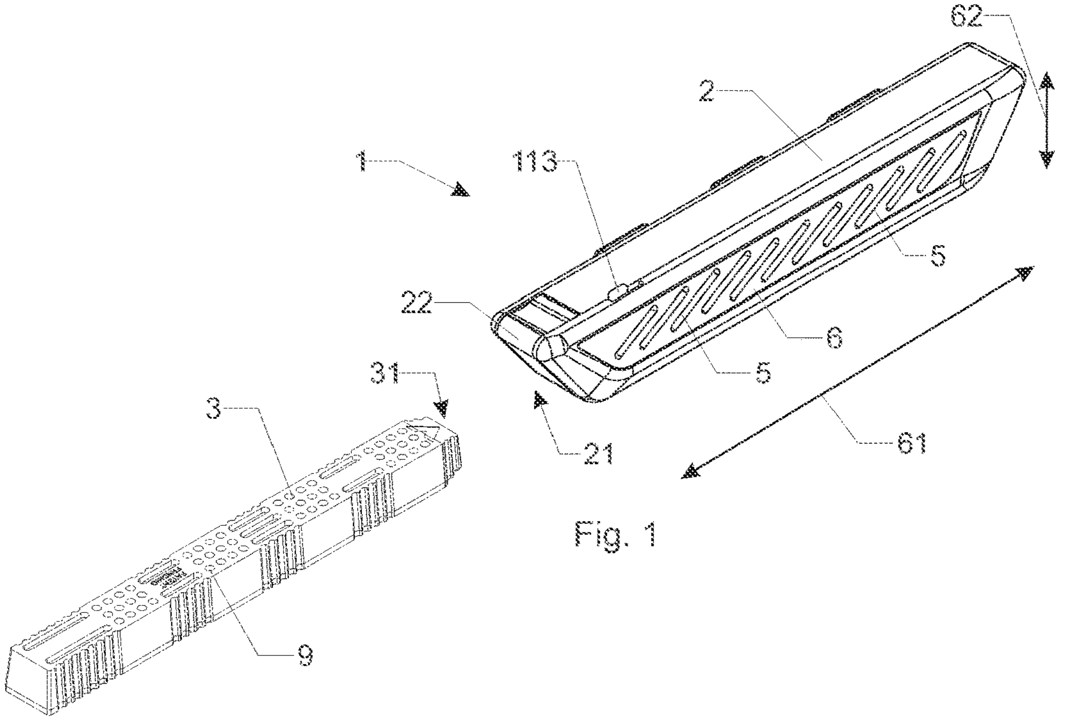
FIG. 1 a scenting device with a view of the front and a scent container which has not been inserted.

FIG. 1 shows the front side of the scenting device 1. Outlet openings 5 are arranged at the front of the scenting device 1. The front side is therefore also referred to as the outlet side 6. In addition, outlet openings may also be provided on one or both side walls of the housing 2 and/or on its top side and/or on its bottom side.

Figure 2:
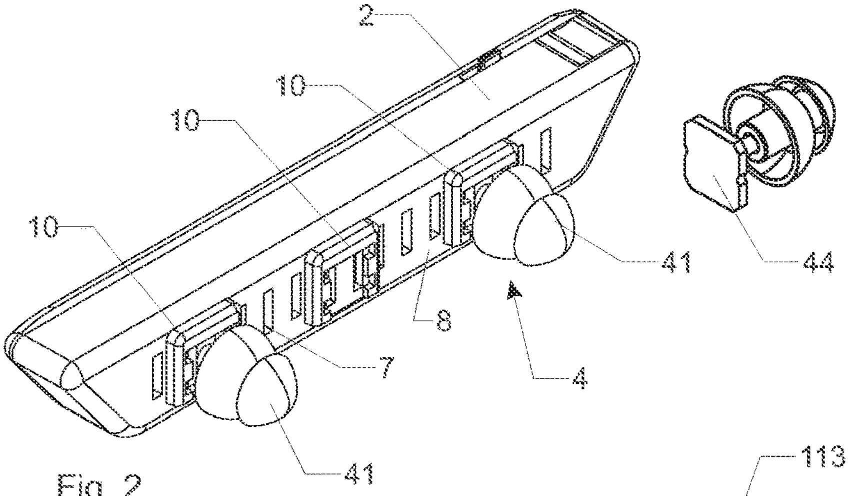
FIG. 2 the scenting device with a view of the rear side, whereby two rubber caps are coupled to the scenting device.
Figure 3:
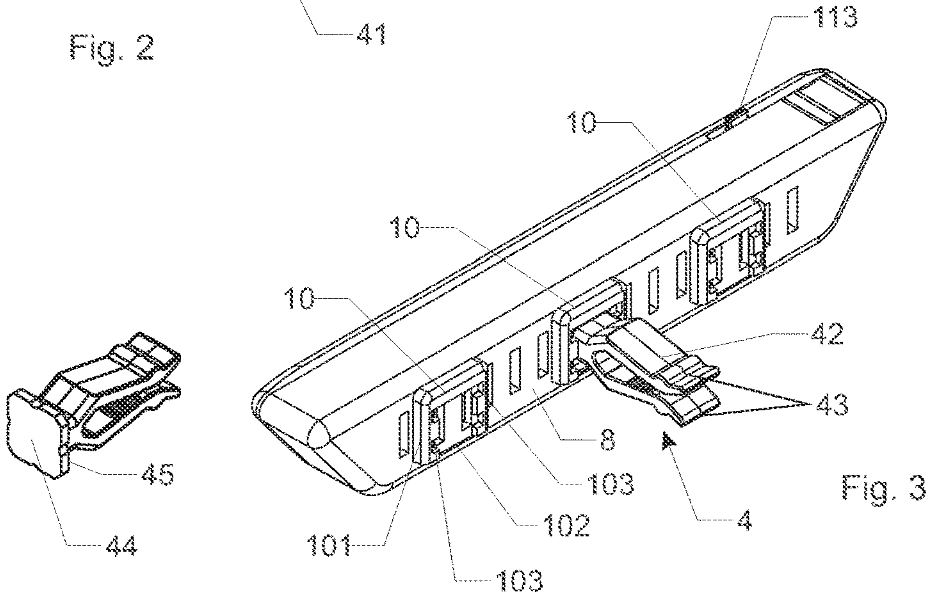
FIG. 3 the rear view of the scenting device with a spreader element coupled to the scenting device.

FIGS. 2 and 3 show the scenting device 1 as seen from the rear. Inlet openings 7 are arranged at the rear of the scenting device 1. The rear side is therefore also referred to as the inlet side 8.

If the scenting device 1 is mounted on the ventilation in the passenger compartment of the vehicle, the inlet side 8 is directed towards the ventilation and the outlet side 6 is directed away from the ventilation. Air flows out of the ventilation through the inlet openings 7, into the housing 2 and into the scent container 3 arranged in the housing 2. The air comes into contact with the scent in the scent container 3, is enriched with scent molecules and leaves the housing 2 of the scenting device 1 through the outlet openings 5. The air reaches the interior of the vehicle and scents the interior.

Scent Container

The scent container 3, as shown in FIG. 2, is provided as a replaceable scent stick, wherein the scent stick comprises as material a composite material of at least one polymer, in particular an elastomer, and the scent, or consists of such a material. In this case, the polymer is enriched with the scent and acts as its carrier. Preferably, the scent stick has a plurality of passage openings 9 through which the air emerging from the ventilation slot can flow. By providing the passage openings 9, the surface area is increased at which the air exiting the ventilation slot comes into contact with the scent, which results in an increased enrichment of the air flowing through the scenting device 1 with scent molecules. The passage openings 9 are preferably aligned with the direction of flow of the air from the ventilation slot. Alternatively, the scent may be provided in the form of granules contained in a cage.

As shown in FIG. 1, the housing 2 has a housing opening 21 at one of its ends, which can be closed with a housing cover 22. To replace the scent container 3, the user opens the housing cover 22, which is attached to the housing by a rotary hinge and thus remains connected to the housing 2 even in the open position.

If the user wants to insert the new scent container 3, he must insert it in the correct direction into the housing 2 and into a sliding container 11. This is because a recess 31 is provided at the front end of the scent container 3, in which a protrusion of the housing 2 or of the sliding container 11 engages in the inserted position. If the recess 31 and the protrusion do not engage, the scent container 3 cannot be fully inserted into the housing 2 and the housing cover 22 cannot be closed. Once the user has correctly inserted the scent container 3 into the housing 2, he can close the housing cover 22. When closing, the housing cover 22 locks into place on the housing 2 so that the housing cover 22 does not open unintentionally.

Figure 4:
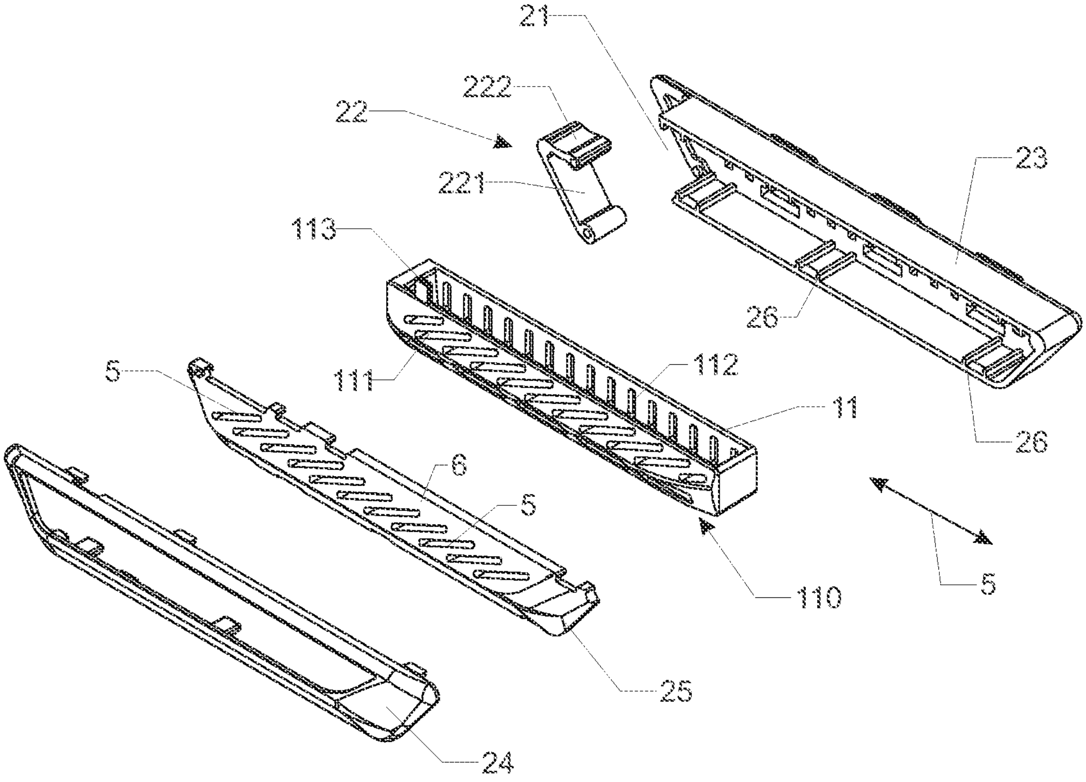
FIG. 4 an exploded view of the scenting device without the scent container.
Figure 5A:
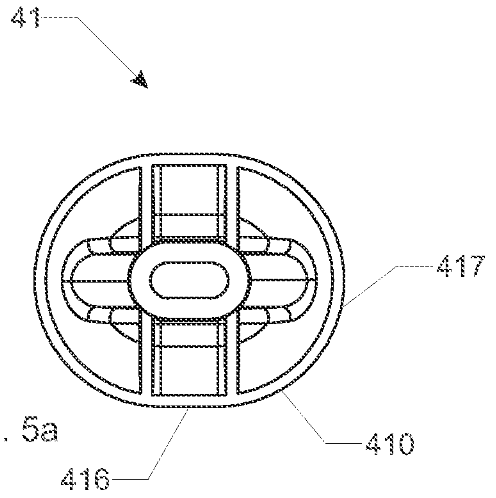
FIGS. 5*a* to 5*f* a rubber cap in different views.
Figure 5B:
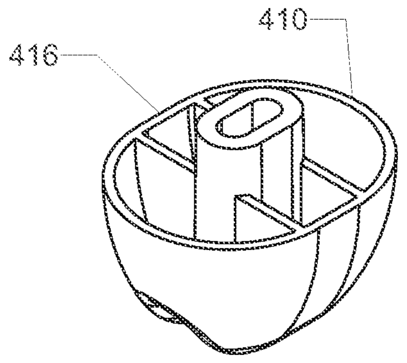
Figure 5C:
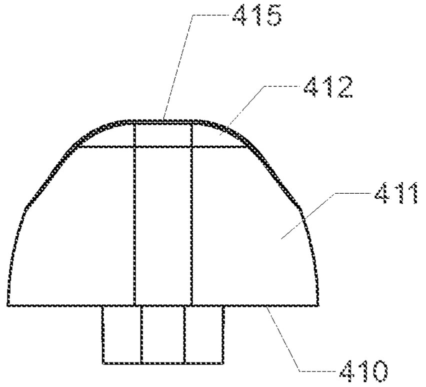
Figure 5D:
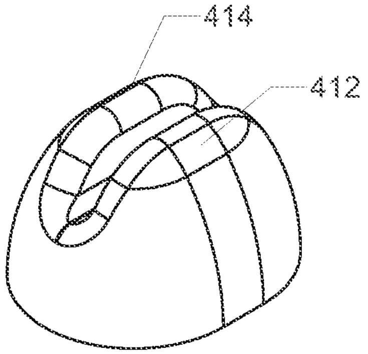
Figure 5E:
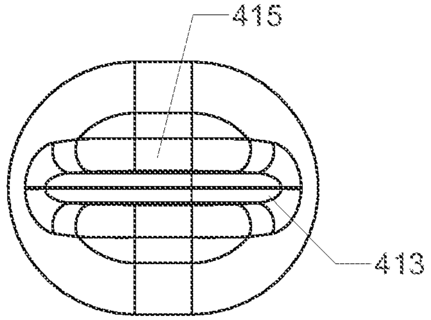
Figure 5F:
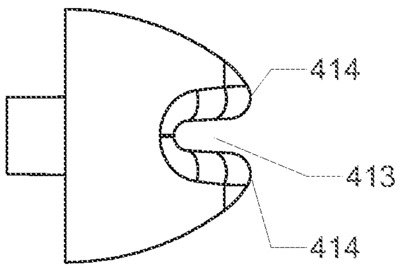

It is clearly visible in FIG. 4 that the housing cover 22 has a curved shape. The longer section 221 of the housing cover 22 forms the lateral end of the housing 2. The shorter section 222 of the housing cover 22 extends along a section of the longitudinal side of the housing 2. The curved shape of the housing cover 22 has the advantage that the housing opening 21 is correspondingly large and the scent container 3 can be conveniently inserted.

Design of the Outlet Side

As shown in FIG. 1, the housing 2 and thus also the outlet side 6 has an elongated shape with a long side 61 and a short side 62. Several outlet openings 5 are arranged on the outlet side 6. They each have the shape of an elongated slot and are arranged parallel and equidistant to each other.

The outlet openings 5 are each arranged obliquely to the long side 61 and obliquely to the short side 62. In other words, the outlet openings 5 are arranged neither parallel to the longitudinal side 61, nor parallel to the short side 62. In the present embodiment, oblique means that the outlet openings 5 designed as slots are arranged at an angle of 45° to the long side 61 and at an angle of 45° to the short side 62. The outlet openings 5 each extend approximately over the entire length of the short side 62.

Holding Devices

Three coupling devices 10 are arranged on the inlet side 8. A holding device 4 can be coupled to each of the three coupling devices 10. The three coupling devices 10 are spaced apart and inlet openings 7 are arranged between them.

FIG. 2 shows a first variant for mounting the air freshener 1 on the vehicle's ventilation. A holding device 4 with a rubber cap 41 is coupled to each of the outer coupling devices 10. The middle coupling device 10 is left free and is not coupled to any holding device 4.

The rubber caps 41 are made of a resilient material and are configured to be clamped between two slats of the ventilation in the vehicle. The holding devices 4 with the rubber caps 41 can thus be inserted in a holding manner into a ventilation slot in the vehicle interior. In other words, the dimensions of the rubber caps 41 are determined in dependence on the dimensions, in particular the width, of the ventilation slot in such a way that the air freshening device 1 can be attached to the ventilation slot by inserting/inserting the rubber caps 41 into the ventilation slot where they are held in a clamping manner by the latter. The rubber caps 41 are attachable to the holding devices 4. This allows the rubber caps 41 to be replaced in a simple manner.

The housing 2 is preferably elongated. If it is mounted on a ventilation slot, it extends along the ventilation slot. Both holding devices 4 are arranged in the same ventilation slot. Of course, it is also possible to arrange the housing 2 transversely to the ventilation slots, in which case the holding devices 4 are placed in different ventilation slots.

FIG. 3 shows a second variant for mounting the air freshener 1 on the vehicle's ventilation. The outer coupling devices 10 are left free and are not coupled to any holding device 4. Only on the middle coupling device 10 is a holding device 4 arranged, which has a spreader element 42. The spreader element 42 comprises two spreader members 43 and can be clamped between two slats of the vehicle's ventilation like the rubber caps 41.

The holding device 4 with the rubber cap 41 and the holding device 4 with the spreader element 42 represent different types of holding devices 4, which are structurally different.

All three coupling devices 10 are identically designed. That is, both the holding devices 4 with the rubber caps 41 and the holding device 4 with the spreader element 42 can be coupled to all three coupling devices and thus be interchangeable with each other. According to the claims, each of the holding devices 4 can thus be coupled to one of the at least one coupling device 10.

As shown in FIGS. 2 and 3, the coupling devices 10 couple to the holding devices 4 in the form of a snap-fit. The coupling devices 10 comprise a square frame 101. The frame 101 is closed on three sides and has a frame opening 102 on its underside. The frame 101 also has two gaps 103 arranged on each of the left and right sides.

The holding device 4 comprises a flat, square plate 44 to which either the rubber caps 41 or the spreader element 42 are connected, depending on the type of holding device 4. Protrusions 45 are arranged on the plate 44, which can engage in the gaps 103 of the frame 101 of the coupling device 10 in a snapped-in position.

A user can couple the holding device 4 to the coupling device 10 by pushing the plate 44 of the holding device 4 from the underside through the frame opening 102 below the frame 101. In doing so, the frame 101 deforms elastically because the protrusions 45 press on the frame 101. The user pushes the plate 44 further until the protrusions 45 appear in the gaps 103. The frame 101 deforms back and the plate 44 is snapped into the frame 101. Holding device 4 and coupling device 10 are coupled together.

If a user wishes to uncouple the holding device 4 from the coupling device 10, the user moves the holding device 4 downwards so that the plate 44 is guided out of the frame 101 through the frame opening 102. The user must apply a certain amount of force for this movement, i.e., for the disengagement of the snap-fit, as the frame 101 again deforms elastically due to the protrusions 45.

As already described, different variants are available to the user for mounting the air freshener 1 to the ventilation in the vehicle. On the one hand, the user can use the holding devices 4 with the rubber caps 41 for mounting, on the other hand, the holding device 4 with the spreader element 42. The user thus has a kit which comprises, on the one hand, the housing 2 with the scent container 3 and, on the other hand, the different types of holding devices 4. In addition, the kit may also include rubber caps 41 of different sizes. I.e., in this case the user has a total of three variants at his disposal for mounting the scenting device 1 on the ventilation in the interior of the vehicle. The mounting is carried out by means of the smaller rubber caps 41, by means of the larger rubber caps 41 or by means of the spreader element 42. The user chooses from the three variants the one which is best suited for mounting the scenting device 1 depending on the design of the ventilation.

Sliding Device

FIG. 4 shows an exploded view of the individual parts of the scenting device 1. The scent container 3 is not visible. The housing 2 comprises a rear housing cover 23, a front housing frame 24 which frames a front housing cover 25. The housing cover 25 includes the aforementioned outlet openings 5 on the outlet side 6. Also shown is the aforementioned housing cover 22, which can close the housing opening 21.

A sliding device with a sliding container 11 is arranged inside the housing 2. The sliding container comprises a bottom 110, a front wall with inclined outlet openings 111 and a rear wall with vertical inlet openings 112. There is space between the walls of the sliding container 11 so that the scent container 3 can be arranged inside the sliding container 11.

On the inside of the housing 2, there are webs 26 on which the sliding container 11 rests on the bottom or which it touches with its side walls. This keeps the touching area between the housing 2 and the sliding container 11 as small as possible. The sliding container 11 can be easily moved within the housing 2.

To move the sliding container 11, a plate-shaped handle 113 is arranged on its upper side, which protrudes from the housing 2 through the upper side of the housing 2. The handle 113 thus does not protrude through either the inlet side 8 or the outlet side 6. The handle 113 is also visible in FIG. 1. By actuating the handle 113, the user can move the sliding container 11 longitudinally relative to the housing 2. The sliding container 11 is thereby moved back and forth in the direction of the double arrow 114 shown in FIG. 4.

Since the scent container 3 is arranged within the sliding container 11 and does not touch the housing 2, the scent container 3 moves in the same manner as the sliding container 11 relative to the housing 2. As a result, the scent container 3 does not rub against the housing 2 during the movement. Friction only occurs between the sliding container 11 and the webs 26 of the housing 2. The movement thus occurs in a controlled manner, with only slight friction, and is independent of whether the scent container 3 has been correctly inserted into the sliding container 11 by the user.

By means of the movement of the sliding container 11, the user can open and close the inlet openings 7 and the outlet openings 5. In the closed state, the struts of the sliding container 11 cover the inlet openings 7 and the outlet openings 5. Air cannot flow through the scenting device 1. In the open state, the outlet openings 111 of the sliding container 11 are congruent with the outlet openings 5 of the housing 2 and the inlet openings 112 of the sliding container 11 are congruent with the inlet openings 7 of the housing 2. Air can flow through the scenting device 1 and be enriched with scent molecules of the scent container 3.

Design of the Rubber Caps

FIGS. 5*a* to 5*f* show the rubber caps 41 arranged on the holding devices 4 in detailed view and from different perspectives. The rubber cap 41 has a base surface 410, an outer surface 411 and an upper surface 412 opposite the base surface 410. Since the rubber cap 41 shown in FIG. 6 has a rounded upper surface 412, the upper surface 412 forms part of the outer surface 411.

The base surface is the surface of the rubber cap which, in the assembled state, faces the housing of the scenting device. The upper surface is the surface of the rubber cap which, in the assembled state, is directed away from the housing of the scenting device.

An elongated groove 413 is arranged on the upper surface 412 of the rubber cap 41. The groove 413 separates the upper surface 412 into two parallel upper edges 414, each of these upper edges 414 having a rectilinear section 415.

The base 410 of the rubber cap 41 has a perimeter or an edge line with two rectilinear sections 416. These two rectilinear sections 416 are joined by two semicircles 417.

The base 410 thus resembles an elliptical shape, although it is precisely not an elliptical shape because the rim line has rectilinear sections 416.

While preferred embodiments of the invention are described in the present application, it should be clearly noted that the invention is not limited to these and may also be carried out in other ways within the scope of the following claims.

The invention claimed is:

1. A scenting device for a vehicle, the scenting device comprising:
- a housing,
- a scent container arranged in the housing,
- one or more coupling devices arranged on the housing,
- one or more holding devices configured to attach the scenting device to a ventilation in the interior of the vehicle,
- wherein at least one or the one or more holding devices is configured to be coupled to and decoupled from at least one of the one or more coupling devices,
- wherein the at least one or more holding devices has a rubber cap,
- wherein the rubber cap is adapted to be clamped between two slats of the ventilation, and/or is removable from the at least one of the one or more holding devices,
- wherein the rubber cap has an outer surface, a base surface, and a upper surface opposite the base surface; and
- wherein an edge line of the base surface has at least two rectilinear sections, wherein the edge line comprises two semicircles or half-ellipses connecting the two rectilinear sections.

2. The scenting device according to claim 1, wherein at least one of said holding devices comprises a spreader element,
- wherein the spreader element is configured to be clampable between two slats of the ventilation.

3. A scenting device for a vehicle, the scenting device comprising:
- a housing,
- a scent container arranged in the housing,
- one or more coupling devices arranged on the housing,
- one or more holding devices configured to attach the scenting device to a ventilation in the interior of the vehicle,
- wherein at least one of the one or more holding devices is configured to be coupled to and decoupled from at least one of the one or more coupling devices,
- wherein the at least one of the one or more holding devices has a rubber cap,
- wherein the rubber cap is adapted to be clamped between two slats of the ventilation, and/or is removable from the at least one of the one or more holding devices,
- wherein at least another one of said one or more holding devices comprises a spreader element,
- wherein the spreader element is configured to be clampable between two slats of the ventilation and/or comprises at least two spreader members, and
- wherein the at least one of the one or more holding devices is configured to be coupled to the rubber cap and the at least another one of the one or more holding devices is configured to be coupled to the spreader element on each of the one or more coupling devices.

4. The scenting device according to claim 3, wherein the one or more coupling devices include exactly three coupling devices arranged on the housing, including a first coupling device, a second coupling device, and a third coupling device, wherein the first coupling device is arranged in a middle between the second coupling device and the third coupling device, in particular wherein only the first coupling device arranged in the middle is coupled to the one or more holding devices, or only the second and third coupling devices are coupled to the one or more holding devices.

5. The scenting device according to claim 4, wherein the first coupling device in the middle is coupled to the another one or more holding devices with the spreader element, and none of the one or more holding devices is coupled to the second or third coupling devices.

6. The scenting device according to claim 4, wherein both the second coupling device and the third coupling device are each coupled to one of the one or more holding devices with the rubber cap.

7. The scenting device according to claim 6, wherein no holding device is coupled to the first coupling device.

8. The scenting device according to claim 3, wherein the scenting device includes at least three coupling devices arranged on the housing, and wherein the scenting device includes at least three holding devices, wherein each of the at least three holding devices are configured to be coupled to and decoupled from a corresponding one of the at least three coupling devices, wherein the at least three coupling devices are spaced apart from one another, and/or wherein inlet openings are provided between the at least three coupling devices, through which air can flow into the housing.

9. The scenting device according to claim 3, wherein the one or more coupling devices and the one or more holding devices are adapted such that they couple with one another in the form of a snap-fit.

10. The scenting device according to claim 3, wherein each of the one or more coupling devices comprises a frame and each of the one or more holding devices comprises a flat plate configured such that the flat plate of each of the one or more holding devices is configured to be slid under the frame of a corresponding one of the one or more coupling devices for coupling, wherein the each flat plate has at least one protrusion which engages in gaps of the frame in the coupled position.

11. The scenting device according to claim 3, wherein the scenting device comprises at least two holding devices with the rubber caps, wherein the at least two holding devices comprise rubber caps of different sizes.

12. The scenting device according to claim 3, wherein the rubber cap has an outer surface, a base surface and an upper surface opposite the base surface.

13. The scenting device according to claim 12, wherein a groove is arranged on the upper surface of the rubber cap and/or wherein two upper edges running parallel are arranged on the upper surface of the rubber cap, wherein the two upper edges each have a rectilinear section.

* * * * *